United States Patent [19]

Ford

[11] Patent Number: 4,954,128
[45] Date of Patent: Sep. 4, 1990

[54] THERAPEUTICS PLASMA EXCHANGE SYSTEM

[75] Inventor: Michael G. Ford, Riverside, Calif.

[73] Assignee: Baxter International Inc., Deerfield, Ill.

[21] Appl. No.: 235,056

[22] Filed: Aug. 23, 1988

[51] Int. Cl.$^5$ .............................................. A61M 1/38
[52] U.S. Cl. ........................................ 604/5; 210/927
[58] Field of Search ................. 210/259, 927; 604/4–6

[56] References Cited

U.S. PATENT DOCUMENTS

| | | |
|---|---|---|
| Re. 31,688 | 9/1984 | Popovich et al. |
| 4,637,813 | 1/1987 | De Vries .................................. 604/6 |
| 4,648,866 | 3/1987 | Malbrancq ............................... 604/5 |
| 4,776,964 | 10/1988 | Schoendorfer et al. |

FOREIGN PATENT DOCUMENTS

WO85/04112 9/1985 PCT Int'l Appl.

*Primary Examiner*—Stephen C. Pellegrino
*Attorney, Agent, or Firm*—June M. Bostich; Bradford L. Price

[57] ABSTRACT

The system includes a plasmapheresis instrument and a harness set applied to the instrument. The harness set has a single venepuncture needle and is configured, when applied to the instrument, to pump blood from a donor through a separator for collection of its constituent parts in a reservoir and a collection container, respectively. During an infusion cycle, which alternates with the collection cycle, the blood constituent from the reservoir and a replacement fluid are mixed externally of the reservoir and pumped to the donor.

15 Claims, 3 Drawing Sheets

COLLECTION CYCLE

COLLECTION CYCLE

INFUSION CYCLE

THERAPEUTICS PLASMA EXCHANGE SYSTEM

BACKGROUND OF THE INVENTION

The present invention relates to apparatus for and methods of therapeutic plasma exchange wherein blood is collected from a donor and separated into constituent parts, and the donor is infused with a combination of at least one of the separated constituent parts and a replacement fluid. More particularly, the present invention relates to a single needle therapeutic plasma exchange system for alternately collecting blood from a donor and infusing the donor with a separated constituent part of the collected blood and a replacement fluid.

Automated plasmapheresis systems designed to collect a volume of whole blood from a donor, separate the blood into constituent parts, and reinfuse the donor with one of the constituent parts, e.g., packed cells, are well known. One such plasmapheresis system includes an Autopheresis-C ™ instrument designed for use with a disposable harness set. The harness set includes a single venepuncture needle, a separator, various tubing runs and ancillary equipment. When the set is applied to the instrument and the needle is applied to the donor, the system alternates between a whole blood collection cycle and a reinfusion cycle wherein the donor is reinfused with the residual red cell concentrate. To accomplish this, the system uses pumps, sensors, clamps, transducers and other instrumentation under computer control. The donor remains connected to the system during both collection and infusion cycles until the process is completed. The system employs a membrane filter as part of the harness set and the filter yields rapid and gentle separation of whole blood into constituent parts for reinfusion and virtually cell-free plasma for collection.

More particularly, in the collection cycle of such system, whole blood is drawn from the donor through the single venepuncture needle and enters the harness set. Anticoagulant solution is pumped at a controlled rate into the blood entering the harness set. Anticoagulated whole blood is then pumped to a membrane separator, where the plasma and red cells are separated. The plasma is then passed into a collection container and the packed cells are pumped from the separator to a reservoir for subsequent reinfusion. Sensors detect the level of red cells in the reservoir and, when filled, the computer control then terminates the collection cycle and initiates the reinfusion cycle. Packed cells are then pumped from the reservoir back to the donor via the single needle. The reinfusion cycle continues until the reservoir is substantially emptied of packed cells. At that time, the system cycles to the collection cycle and continues to alternate collection and infusion cycles until a predetermined volume of plasma has been collected, at which time the system stops.

The present invention provides apparatus and methods for therapeutic plasma exchange in general and also extends the application of the aforedescribed instrument to therapeutic plasma exchange, although it will be recognized that the present invention may be useful with any fluid filtering and/or processing system wherein an input fluid is separated and infusion of a replacement fluid together with a part of the separated fluid is desired, e.g., blood processing applications.

According to the present invention, there is provided a harness set specifically configured for separation and exchange or replacement systems, i.e., a therapeutic plasma exchange system, and, more particularly configured for use with the plasmapheresis instrument previously described. The harness set preferably includes a single venepuncture needle, a plasma membrane separator, a reservoir, a fluid replacement container, an anticoagulant container and a plasma collection container. These various elements are connected by various tubing runs, i.e., lines or conduits. Thus, when the harness set is applied to the instrument, blood may be withdrawn from the donor through the venepuncture needle. An anticoagulant is added to the blood and the anticoagulated blood flows through the separation device, where it is separated into blood constituents, i.e., a plasma and packed cells. The plasma flows to the plasma collection bag and the packed cells flow to the reservoir. The harness set is constructed for application to the instrument such that, during the collection cycle, the blood collection pump pumps blood from the donor to the separator and the cell pump pumps packed cells into the reservoir.

When a predetermined quantity of packed cells have been stored in the reservoir, the collection cycle is terminated and an infusion cycle is initiated to mix the packed cells and the replacement fluid one with the other and return those fluids to the donor through the single venepuncture needle. During the infusion cycle, the cell pump pumps and meters replacement fluid from the replacement container through the separator for mixing with the packed cells from the reservoir whereby the combined packed cells and replacement fluid flow to the donor through the venepuncture needle. The ratio of the replacement fluid rate to the packed red cell rate returned to the donor can be controlled from zero to a desirable maximum. That maximum is defined such that the replacement rate does not exceed the blood pump rate so that flow of replacement fluid into the reservoir is avoided. This ensures that the optical sensors on the instrument for determining the packed cells level in the reservoir remain effective. It will be appreciated that the optical sensors provide input to the computerized instrument control to advance the system from the collection cycle to the infusion cycle when the reservoir is filled with packed cells and, when the reservoir is emptied of packed cells, to end the infusion cycle and begin the next collection cycle.

In a preferred embodiment hereof in accordance with the present invention, there is provided a plasma exchange system for separating blood received from a donor into constituents and infusing the donor with a first blood constituent and a replacement fluid, the system being comprised of a separator for separating first and second blood constituents from whole blood, a reservoir for containing blood and having a single port and a single venepuncture needle for supplying whole blood from the donor to the separator during a whole blood collection cycle and infusing the donor with a blood constituent and a replacement fluid during an infusion cycle. Means are provided for supplying a first blood constituent from the separator through the port to the reservoir during a collection cycle, the means including the single venepuncture needle in communication with the reservoir through the port for flowing the first blood constituent in the reservoir to the donor during the infusion cycle. Also provided is a fluid replacement supply source and means in communication with the fluid replacement supply source and flow means for supplying replacement fluid to the donor during the infusion cycle.

In a further preferred embodiment of the present invention, there is provided a method for separating blood received from a donor into constituents and infusing a donor with a first blood constituent and a replacement fluid, comprising the steps of supplying whole blood from a donor to a separator during a blood collection cycle, separating the whole blood into constituents and storing at least a first blood constituent in a reservoir for reinfusion into the donor and, during an infusion cycle, pumping replacement fluid through the separator, pumping the first blood constituent from the reservoir, mixing the first blood constituent pumped from the reservoir and the replacement fluid from the separator one with the other, and infusing the donor with the combined first blood constituent and the replacement fluid.

Accordingly, it is a primary object of the present invention to provide novel and improved apparatus and methods for therapeutic plasma exchange wherein whole blood may be separated into constituent parts and one of such parts may be readily and easily combined with a replacement fluid for infusing the donor.

These and further objects and advantages of the present invention will become more apparent upon reference to the following specification, appended claims and drawings.

BRIEF DESCRIPTION OF THE DRAWING FIGURES

FIG. 1 is a perspective view of the front face of a plasmapheresis instrument with a harness set, constructed according to the present invention, applied to the face of the instrument; and FIGS. 2 and 3 are schematic views of the flows in the system during the collection and infusion cycles, respectively.

DETAILED DESCRIPTION OF THE DRAWING FIGURES

Reference will now be made in detail to the present preferred embodiment of the invention, an example of which is illustrated in the accompanying drawings.

Figure 1:
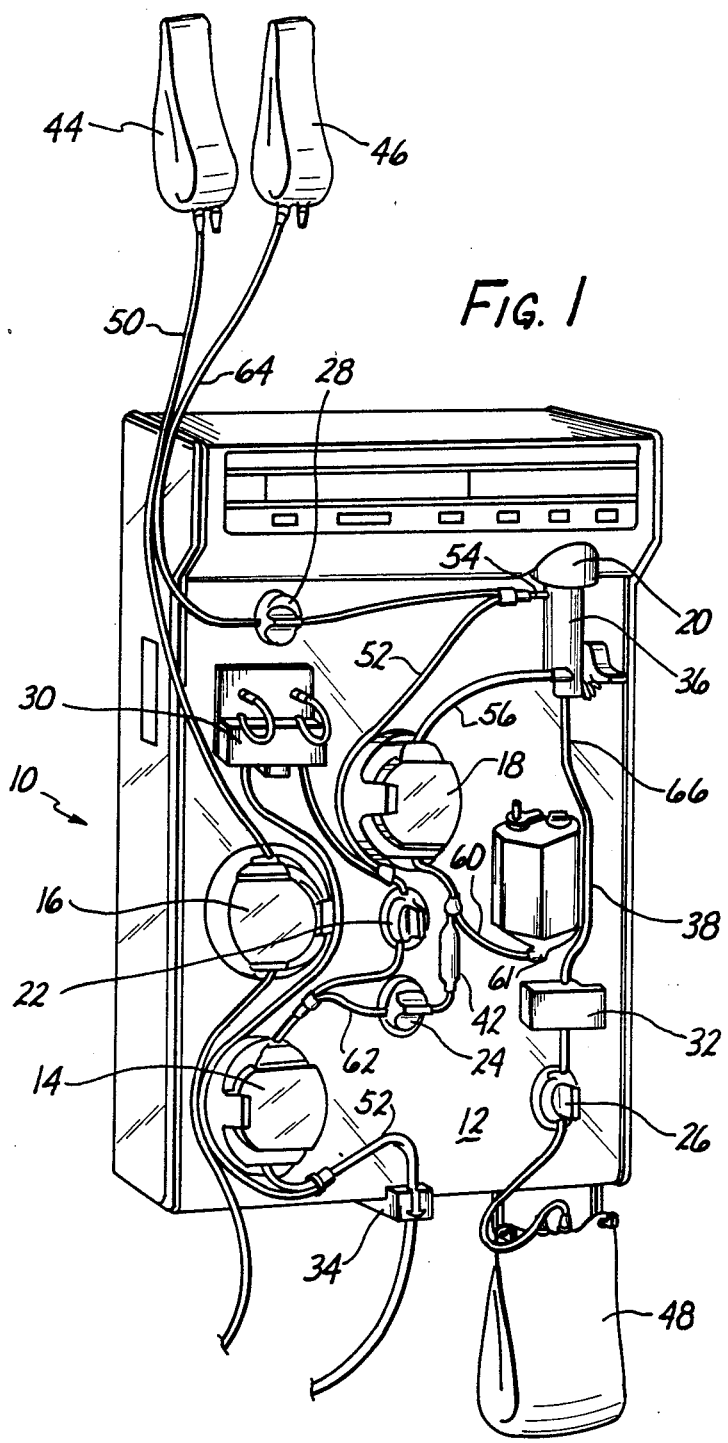

A conventional plasmapheresis instrument is generally designated 10 in FIG. 1 and includes various pumps, clamps, detectors, monitoring systems, transducers, indicators and the like, not all of which are described in the present application or necessary to an understanding of the present invention. Therefore, only those parts of the instrument which are applicable for an understanding of the present invention will be described.

Instrument 10, on its face 12, includes three peristaltic pumps which are individually driven and under the control of a computerized control system. A blood pump 14 is provided for delivering anticoagulated whole blood from the donor to a separator, described hereinafter, during the collection cycle and for pumping a blood constituent and replacement fluid to the donor during the infusion cycle. An anticoagulant pump 16 is provided for pumping anticoagulant into the whole blood as the blood enters the harness set. A cell pump 18 is operable during the blood collection cycle to pump the separated blood constituent from the separator to the reservoir. In accordance with the present invention, during the infusion cycle, cell pump 18 pumps the replacement fluid from the replacement fluid container and through the separator for mixing with packed cells from the reservoir whereupon blood pump 14 pumps, in the reverse direction from the collection cycle, the mixture of the packed cells and replacement fluid to the donor. A magnetic motor mount 20 for the separator is also provided on the instrument face 12. The various clamps include a blood line clamp 22, a reinfusion line clamp 24, a plasma line clamp 26 and a replacement fluid clamp 28. Additional elements shown on the face of instrument 10 include a pressure transducer assembly 30, a hemoglobin detector 32 and an ultrasonic air detector 34. These latter elements are not pertinent to an understanding of the present invention.

A disposable harness set, according to the present invention, is applied to the instrument and to the donor such that blood collection, separation and infusion of packed cells with replacement fluid may be provided. The harness set includes a membrane separation device 36 for separating whole blood into plasma and packed cells, a reservoir 38 for receiving the packed cells, a single venepuncture needle 40 (see FIGS. 2 and 3), an in-line filter 42, an anticoagulant supply container 44, a replacement fluid supply container 46, a plasma collection container 48 and various tubing runs, lines or conduits which will be described hereinafter. The construction of the separator 36 forms no part of the present invention and reference is made to co-pending U.S. patent application Ser. No. 73,378, filed July 13, 1987 as a continuation of U.S. patent application Ser. No. 591,925, filed Mar. 21, 1984, now abandoned, for a complete description of a separator useful with this invention. The disclosure of application Ser. No. 73,378 is incorporated herein by reference.

Figure 2:
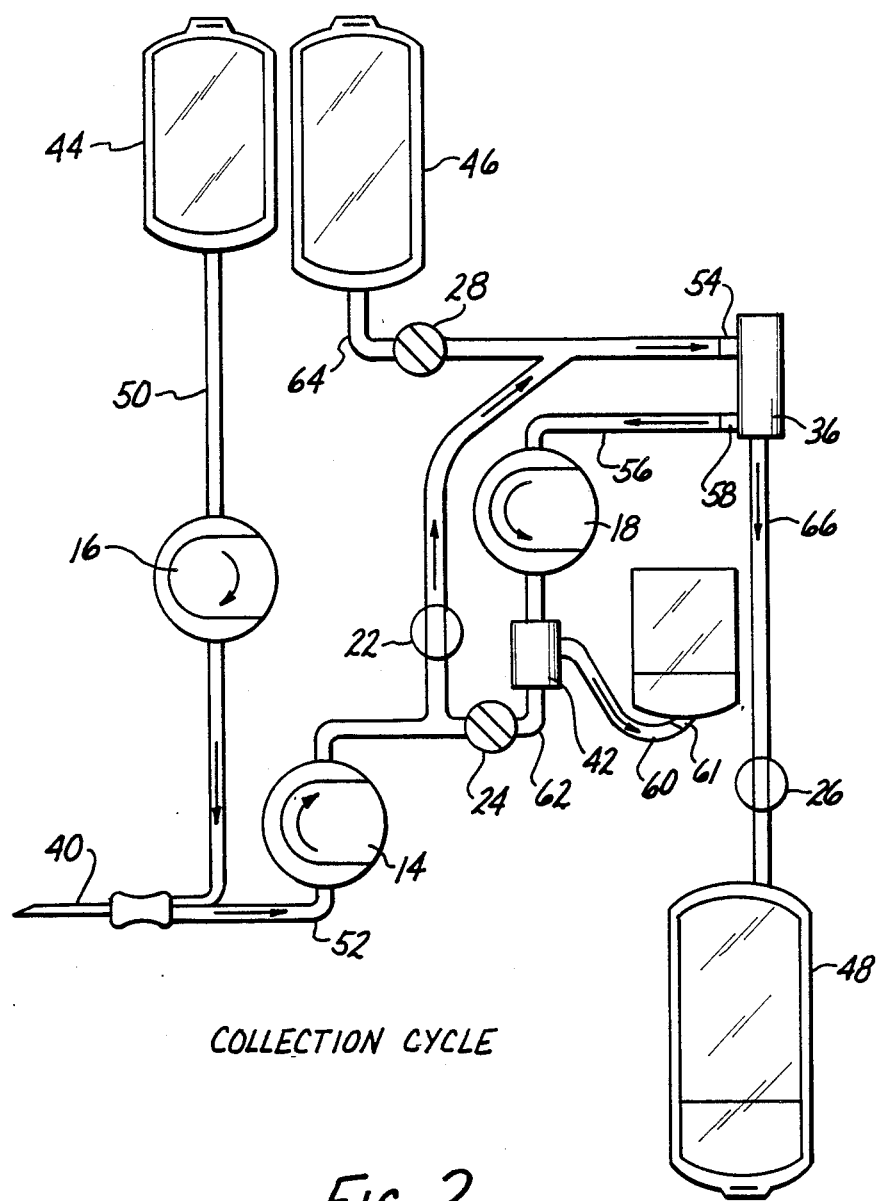
Figure 3:
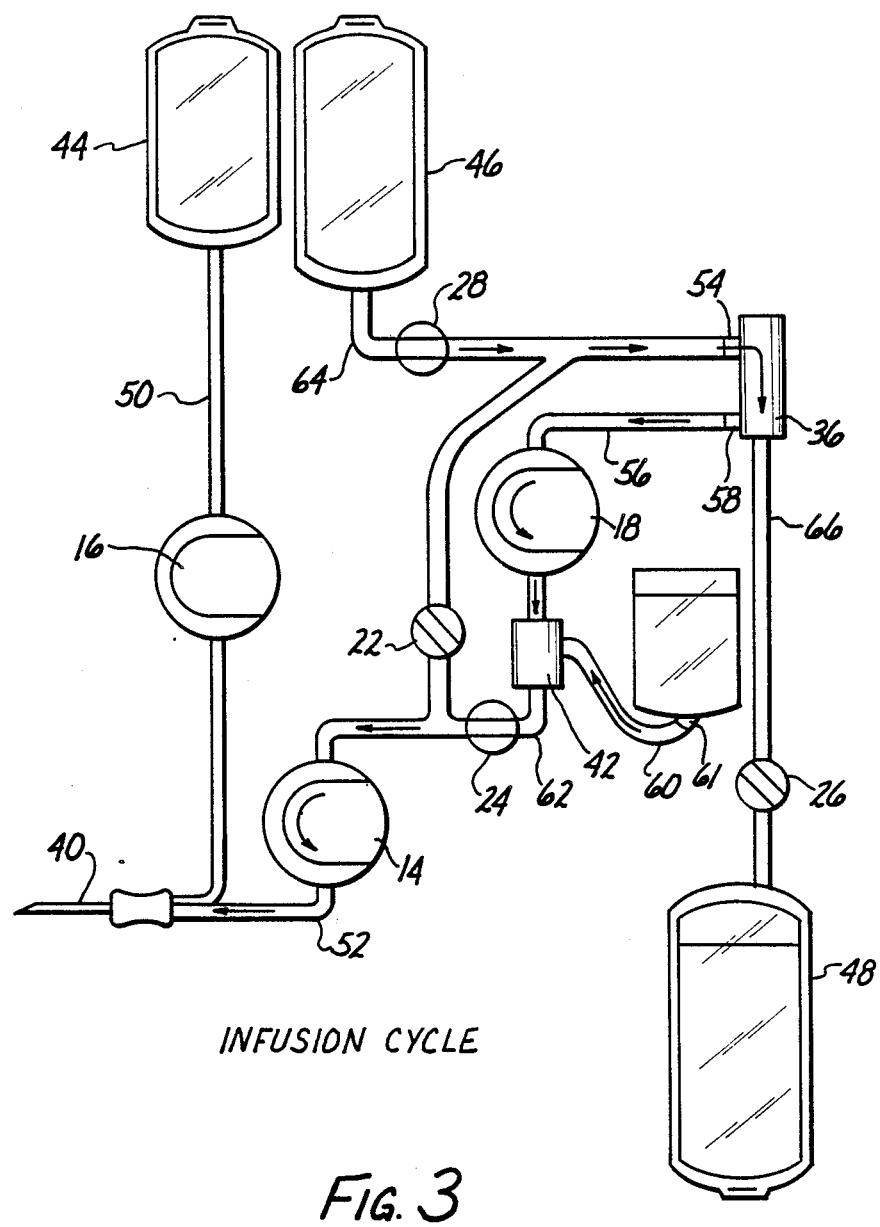

With reference to FIGS. 2 and 3, the various tubing runs will now be described. An anticoagulant line 50 connects anticoagulant supply container 44 with the blood line 52 at a Y-fitting near the phlebotomy needle 40 connection luer, not shown. The blood line 52 connects with the needle 40 and supplies anticoagulated blood to the input port 54 of the separation device 36. The cell line 56 connects at one end with an output port 58 of separator 36 and, at its opposite end, to an in-line filter 42. A branch line 60 connects a port 61 at the bottom of the reservoir 38 with the in-line filter 42. While only a single port is used herein, it will be appreciated that the bottom of the reservoir may have discrete inlet and outlet ports, if desired. A second branch line 62 connects the in-line filter 42 with the blood line 52. A replacement fluid line 64 connects the replacement fluid container 46 with the inlet port 54 of the separator 36 downstream of the Y-connection made therewith by the blood line 52.

It will be appreciated that, in use, the harness set is applied to the face of the instrument 10. Thus, as illustrated in FIG. 1, the separation device 36 is applied to the motor mount 20 and the reservoir is placed in its holder, not shown. The anticoagulant line 50 is loaded into the anticoagulant pump 16, the blood line 52 is loaded into blood pump 14 and onto the lood line clamp 22. The replacement fluid line is placed on the clamp 28. The cell line 56 is loaded into cell pump 18 and branch line 62 is placed on clamp 24. The plasma line 66 is placed on clamp 26 and the containers 44, 46 and 48 are hung from appropriate hooks, not shown, carried on the instrument.

In operation, various set-up and safety procedures are followed and the venepuncture needle is applied to the donor. To initiate a collection cycle, as illustrated in FIG. 2, clamps 28 and 24 are closed, while clamps 22 and 26 are opened. Anticoagulant pump 16 is operated to pump anticoagulant from supply 44 to the blood line 52. Blood pump 14 is operated to pump anticoagulated blood from the donor through line 52 past the inlet port 54 and into separator 36. Separator 36 separates the blood into constituent parts, e.g., red cell concentrate and plasma, and the plasma flows via plasma line 66, past the open clamp 26, into the plasma collection bag 48. The packed cells flow from separator 36 through the outlet port 58 and are pumped along cell line 56 and branch line 60 into the reservoir 38. When the packed cell level in reservoir 38 rises to a predetermined level, the collection cycle is terminated and the infusion cycle is initiated. When changing over to the infusion cycle, clamps 22 and 26 are closed, clamping off the blood line 52 and plasma line 66, and clamps 24 and 28 are opened. Anticoagulant pump 16 is stopped. Blood pump 14 is reversed such that the packed cells from reservoir 38 are suctioned to flow through the single outlet port 61, along branch lines 60 and 62, past filter 42, and through blood line 52 for return to the donor through the needle 40. Simultaneously, the cell pump 18 is maintained in its running condition, pumping replacement fluid from replacement bag 46 via line 64, separator 36 and line 56 into filter 42.

At the juncture of the cell line 56 and branch conduit 60 adjacent the top of the in-line filter, the replacement fluid mixes with the packed cells drawn by the blood pump 14 from the reservoir 38 via branch lines 60 and 62 and the portion of line 52 between needle 40 and branch line 62. After mixing, the combined packed cells and replacement fluid flow past clamp 24 via line 52 to the donor by way of needle 40.

Note that the juncture of the replacement fluid with the packed cells during infusion is downstream of the reservoir. This assists to prevent replacement fluid from flowing into the reservoir and affecting the optical sensors, not shown, which detect the level of packed cells in the reservoir. Also, it will be appreciated that the replacement fluid rate can be controlled from zero to a desirable maximum less than the blood pump flow rate. In this manner, the replacement fluid is prevented from entering the cell reservoir and this ensures that the optical sensors remain effective and operable to determine the level of red cells in the reservoir. When the reservoir has been substantially depleted of red cells, the control reverts the system back to the collection cycle so that blood collection may begin once again. That is, the control opens clamps 22 and 26, closes clamps 24 and 28, reverses the blood pump 14, actuates anticoagulant pump 16 and continues the operation of the cell pump 18. The collection and infusion cycles thus alternate and it will be appreciated that in each infusion cycle, packed cell and replacement fluid flow simultaneously to the donor in a controlled ratio and in a mixture.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A plasma exchange system for separating blood received from a donor into constituents and infusing the donor with a first blood constituent and a replacement fluid, comprising:
    a separator for separating first and second blood constituents from whole blood;
    a reservoir for containing the first blood constituent and having a single port;
    a single venepuncture needle for supplying whole blood from the donor to said separator during a whole blood collection cycle and infusing the donor with the first blood constituent and a replacement fluid during an infusion cycle;
    means for supplying the first blood constituent from said separator through said port to said reservoir during said collection cycle;
    means including said single venepuncture needle in communication with said reservoir through said port for flowing the first blood constituent in said reservoir to the donor during the infusion cycle;
    a fluid replacement supply source; and
    means in communication with said fluid replacement supply source and said flow means for supplying replacement fluid to the donor during the infusion cycle;
    wherein said means for flowing the first blood constituent to the donor and said means in communication with said fluid replacement supply source lie in communication one with the other for continuously mixing the first blood constituent and the replacement fluid one with the other for simultaneous combined return to the donor.

2. The system according to claim 1 wherein said replacement fluid supplying means and said first blood constituent flow means include discrete flow lines, respectively, and means for controlling the rate of relative flow, with the replacement fluid flow line forming a juncture with said first blood constituent flow line intermediate said port and said venepuncture needle for mixing the replacement fluid and the first blood constituent in the flow line between said juncture and said venepuncture needle for combined flow thereof to the venepuncture needle.

3. The system according to claim 1 wherein said separator forms part of said replacement fluid supplying means during the infusion cycle such that the replacement fluid first flows through said separator and then into said reservoir through said port during the infusion cycle.

4. The system according to claim 2 wherein said flow means includes a filter disposed adjacent the juncture of said replacement fluid flow line and said first blood constituent flow line.

5. Hemapheresis apparatus for separating whole blood collected from a donor into constituents and infusing the donor with a first blood constituent and a replacement fluid, comprising:
    a separator for separating whole blood into first and second blood constituents and having inlet and outlet ports;
    a reservoir having a single port;
    a single venepuncture needle for drawing whole blood from a donor;
    a first conduit connecting said needle and said separator for supplying whole blood from said needle through said inlet port into said separator during a blood collection cycle;
    a second conduit connecting the outlet port of said separator and said reservoir port for supplying the first blood constituent through said single port to said reservoir during the blood collection cycle;

an outlet from said separator for the separated second blood constituent;

a third conduit including portions of said first and second conduits connecting said reservoir and said venepuncture needle for infusing the donor with the first blood constituent;

a fluid replacement supply source; and a fourth conduit connecting said fluid replacement supply source and said separator through said inlet port thereof for supplying replacement fluid to said separator during the blood collection cycle;

whereby, during the blood collection cycle, blood supplied from the donor through said first conduit to said separator may be separated into first and second blood constituents and the first constituent supplied through said second conduit to said reservoir, and during the blood infusion cycle, the first blood constituent may flow from said reservoir through said third conduit to said needle and replacement fluid may flow through said fourth conduit, said separator, and portions of said second and third conduits to said needle, and wherein the first blood constituent and the replacement fluid are continuously mixed in at least a portion of said third conduit for simultaneous combined return to the donor.

6. A system according to claim 5 wherein said second conduit intermediate said separator and said reservoir forms a juncture with said third conduit intermediate said reservoir and said needle for simultaneously mixing the replacement fluid and the first blood constituent during the infusion cycle.

7. A system according to claim 6 including a filter disposed adjacent said juncture.

8. The system according to claim 5 in combination with an autopheresis instrument, said instrument having a face, first and second pumps carried on the face of said instrument, said first and second conduits being disposed in cooperative relation with said first and second pumps, respectively, with sid first pump adapted to pump whole blood from the donor to said separator and said second pump adapted to pump the first blood constituent from said separator to said reservoir, respectively, during said blood collection cycle;

said second pump being cooperable with said second conduit to pump replacement fluid to said third conduit and said first pump being cooperable with said first conduit to pump the first blood constituent from said reservoir through a portion of said second conduit for mixing the first blood constituent and the replacement fluid in the third conduit.

9. The system according to claim 8 wherein said first pump is reversible for pumping first blood constituent during the collection cycle and pumping the mixture of the first blood constituent and the replacement fluid to the donor during the infusion cycle.

10. A plasma exchange system for separating blood received from a donor into constituents and infusing a donor with a first blood constituent and a replacement fluid, comprising:

a separator for separating first and second blood constituents from whole blood;

a reservoir having a top and bottom defining a discrete volume for containing blood and having communicating means adjacent its bottom defining an inlet port for use during a blood collection cycle and an outlet port for use during a blood infusion cycle;

means for supplying whole blood from the donor to said separator during the blood collection cycle;

means for supplying a first blood constituent from said separator to said reservoir through said inlet port during said collection cycle;

a fluid replacement supply source;

means for infusing the donor with the first blood constituent and the replacement fluid during the infusion cycle including means in communication with said reservoir through said outlet port for flowing the first blood constituent in said reservoir to the donor during the infusion cycle; and means in communication with said fluid replacement supply source for supplying replacement fluid to the donor during the infusion cycle.

11. The system according to claim 10 wherein said inlet port and said outlet port constitute the same port.

12. The system according to claim 10 wherein said whole blood supplying means and said infusing means include a single venepuncture needle through which blood is supplied to the separator from the donor during the collection cycle and the first blood constituent and replacement fluid are supplied to the donor during the infusion cycle.

13. The system according to claim 10 including means for mixing the replacement fluid and the first blood constituent during the infusion cycle at a location in said first blood constituent flow means downstream of said reservoir such that said reservoir is maintained free of replacement fluid during both the collection and infusion cycles.

14. A method for separating blood received from a donor into constituents and infusing a donor with a first blood constituent and a replacement fluid, comprising the steps of:

during a blood collection cycle, supplying whole blood from a donor to a separator, separating the whole blood into constituents, and storing at least a first blood constituent in a reservoir for reinfusion into the donor; and during a blood infusion cycle, pumping replacement fluid through the separator, pumping the first blood constituent from the reservoir, mixing the first blood constituent pumped from the reservoir and the replacement fluid from the separator one with the other, and infusing the donor with the combined first blood constituent and the replacement fluid;

wherein the first blood constituent is pumped from the reservoir for infusing the donor at a flow rate greater than the flow rate of the replacement fluid pumped through the separator.

15. The method according to claim 14 including the step of precluding flow of replacement fluid to the reservoir.

* * * * *